United States Patent
Olson

(10) Patent No.: US 6,764,475 B1
(45) Date of Patent: Jul. 20, 2004

(54) ABSORBENT ARTICLES HAVING DIFFERENTIAL STRENGTH REFASTENABLE SEAM

(75) Inventor: Christopher Peter Olson, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/444,632

(22) Filed: Nov. 22, 1999

Related U.S. Application Data

(60) Provisional application No. 60/112,709, filed on Dec. 18, 1998.

(51) Int. Cl.[7] ............................................. A61F 13/15
(52) U.S. Cl. .................. 604/385.03; 604/387; 604/389; 604/391
(58) Field of Search ........................... 604/385.03, 387, 604/389–391, 386; 24/304–306

(56) References Cited

U.S. PATENT DOCUMENTS

| | | |
|---|---|---|
| 2,957,512 A | 10/1960 | Wade et al. |
| 3,039,466 A | 6/1962 | Wilson |
| 3,277,547 A | 10/1966 | Billarant |
| 3,316,139 A | 4/1967 | Alford et al. |
| 3,319,307 A | 5/1967 | Marforio |
| 3,577,607 A | 5/1971 | Ikoma et al. |
| 3,694,867 A | 10/1972 | Stumpf |
| 3,842,832 A | 10/1974 | Wideman et al. |
| 3,842,837 A | 10/1974 | Sward |
| 3,943,981 A | 3/1976 | De Brabander |
| 4,051,854 A | 10/1977 | Aaron |
| 4,122,552 A | 10/1978 | Tedford |
| 4,145,763 A | 3/1979 | Abrams et al. |

(List continued on next page.)

FOREIGN PATENT DOCUMENTS

| | | |
|---|---|---|
| CA | 2096672 | 11/1997 |
| DE | 35 33 881 A1 | 4/1986 |
| DE | 196 54 052 C1 | 12/1997 |
| DE | 197 27 916 A1 | 6/1998 |
| EP | 0 217 032 B1 | 2/1992 |
| EP | 0 520 087 A1 | 12/1992 |
| EP | 0 526 868 A2 | 2/1993 |
| EP | 0 528 282 A2 | 2/1993 |
| EP | 0 321 232 B1 | 5/1993 |
| EP | 0 320 991 B1 | 5/1994 |
| EP | 0 476 992 B1 | 7/1995 |
| EP | 0 487 921 B1 | 9/1995 |
| EP | 0 433 951 B1 | 8/1996 |
| EP | 0 696 911 B1 | 1/1997 |

(List continued on next page.)

OTHER PUBLICATIONS

Advertisement from One Step Ahead® catalog, Late Winter 2000, cover pages and p. 26 referencing "Handy's Training Pants," and a photocopy of a package of Handy's Junior Training Pants as advertised therein.

Primary Examiner—Dennis Ruhl
(74) Attorney, Agent, or Firm—Thomas M. Gage; H. Michael Kubicki

(57) ABSTRACT

A disposable absorbent article has at least one first fastening component disposed in a first waist region and at least one second fastening component disposed in an opposite second waist region. The fastening components are adapted to releasably engage one another and at least one of the fastening components comprises primary and secondary regions that have different releasable engagement properties. Together the fastening components define a refastenable, variable-location seam having a main refastenable attachment zone providing a basic level of securement and an enhanced refastenable attachment zone providing an augmented level of securement.

32 Claims, 5 Drawing Sheets

U.S. PATENT DOCUMENTS

| | | |
|---|---|---|
| 4,201,203 A | 5/1980 | Applegate |
| 4,205,679 A | 6/1980 | Repke et al. |
| 4,209,563 A | 6/1980 | Sisson |
| 4,244,368 A | 1/1981 | Caradonna |
| 4,253,461 A | 3/1981 | Strickland et al. |
| 4,259,957 A | 4/1981 | Sonenstein et al. |
| 4,338,938 A | 7/1982 | Seavitt |
| 4,402,690 A | 9/1983 | Redfern |
| 4,418,123 A | 11/1983 | Bunnelle et al. |
| 4,446,189 A | 5/1984 | Romanek |
| 4,496,360 A | 1/1985 | Joffe et al. |
| 4,516,975 A | 5/1985 | Mitchell |
| 4,560,381 A | 12/1985 | Southwell |
| 4,581,772 A | 4/1986 | Smith |
| 4,585,447 A | 4/1986 | Karami |
| 4,610,680 A | 9/1986 | LaFleur |
| 4,610,682 A | 9/1986 | Kopp |
| 4,615,695 A | 10/1986 | Cooper |
| 4,619,649 A | 10/1986 | Roberts |
| 4,623,339 A | 11/1986 | Ciraldo et al. |
| 4,650,483 A | 3/1987 | Joffe |
| 4,655,760 A | 4/1987 | Morman et al. |
| 4,657,802 A | 4/1987 | Morman |
| 4,662,875 A | 5/1987 | Hirotsu et al. |
| 4,663,220 A | 5/1987 | Wisneski et al. |
| 4,699,622 A | 10/1987 | Toussant et al. |
| 4,701,170 A | 10/1987 | Wilson et al. |
| 4,701,176 A | 10/1987 | Wilson et al. |
| 4,704,116 A | 11/1987 | Enloe |
| 4,705,710 A | 11/1987 | Matsuda |
| 4,714,096 A | 12/1987 | Guay |
| 4,718,901 A | 1/1988 | Singheimer |
| 4,720,415 A | 1/1988 | Vander Wielen et al. |
| 4,725,473 A | 2/1988 | Van Gompel et al. |
| 4,743,239 A | 5/1988 | Cole |
| 4,756,709 A | 7/1988 | Stevens |
| 4,761,318 A | 8/1988 | Ott et al. |
| 4,770,656 A | 9/1988 | Proxmire et al. |
| 4,771,483 A | 9/1988 | Hooreman et al. |
| 4,789,699 A | 12/1988 | Kieffer et al. |
| 4,834,742 A | 5/1989 | Wilson et al. |
| 4,847,134 A | 7/1989 | Fahrenkrug et al. |
| 4,850,988 A | 7/1989 | Aledo et al. |
| 4,850,992 A | 7/1989 | Amaral et al. |
| 4,863,785 A | 9/1989 | Berman et al. |
| 4,894,060 A | 1/1990 | Nestegard |
| 4,895,569 A | 1/1990 | Wilson et al. |
| 4,923,456 A | 5/1990 | Proxmire |
| 4,936,840 A | 6/1990 | Proxmire |
| 4,938,757 A | 7/1990 | Van Gompel et al. |
| 4,940,464 A | 7/1990 | Van Gompel et al. |
| 4,963,140 A | 10/1990 | Robertson et al. |
| 5,019,073 A | 5/1991 | Roessler et al. |
| 5,032,122 A | 7/1991 | Noel et al. |
| 5,046,272 A | 9/1991 | Vogt et al. |
| 5,062,839 A | 11/1991 | Anderson |
| 5,087,253 A | 2/1992 | Cooper |
| 5,104,116 A | 4/1992 | Pohjola |
| 5,114,781 A | 5/1992 | Morman |
| 5,116,662 A | 5/1992 | Morman |
| 5,151,092 A | 9/1992 | Buell et al. |
| 5,176,671 A | 1/1993 | Roessler et al. |
| 5,185,052 A | 2/1993 | Chappell et al. |
| 5,224,405 A | 7/1993 | Pohjola |
| 5,226,992 A | 7/1993 | Morman |
| 5,242,436 A | 9/1993 | Weil et al. |
| 5,256,231 A | 10/1993 | Gorman et al. |
| 5,315,716 A | 5/1994 | Baum |
| 5,318,555 A | 6/1994 | Siebers et al. |
| 5,326,612 A | 7/1994 | Goulait |
| 5,342,341 A | 8/1994 | Igaue et al. |
| 5,370,634 A | 12/1994 | Ando et al. |
| 5,380,313 A | 1/1995 | Goulait et al. |
| 5,383,872 A | 1/1995 | Roessler et al. |
| 5,385,775 A | 1/1995 | Wright |
| 5,399,219 A * | 3/1995 | Roessler et al. ............ 604/389 |
| 5,401,275 A | 3/1995 | Flug et al. |
| 5,407,439 A | 4/1995 | Goulait |
| 5,413,654 A | 5/1995 | Igaue et al. |
| 5,451,219 A | 9/1995 | Suzuki et al. |
| 5,476,702 A * | 12/1995 | Datta et al. ................. 604/391 |
| 5,496,298 A | 3/1996 | Kuepper et al. |
| 5,503,908 A | 4/1996 | Faass |
| 5,527,302 A | 6/1996 | Endres et al. |
| 5,531,731 A | 7/1996 | Brusky |
| 5,531,732 A | 7/1996 | Wood |
| 5,542,942 A | 8/1996 | Kline et al. |
| 5,546,608 A | 8/1996 | Russano |
| 5,547,531 A | 8/1996 | Allen et al. |
| 5,549,591 A * | 8/1996 | Landvogt ..................... 604/389 |
| 5,554,239 A * | 9/1996 | Datta et al. ................. 604/391 |
| 5,569,233 A | 10/1996 | Goulait |
| 5,591,155 A | 1/1997 | Nishikawa et al. |
| 5,595,567 A | 1/1997 | King et al. |
| 5,603,708 A | 2/1997 | Seth |
| 5,605,735 A | 2/1997 | Zehner et al. |
| 5,606,781 A | 3/1997 | Provost et al. |
| 5,611,791 A | 3/1997 | George et al. |
| 5,615,460 A | 4/1997 | Weirich et al. |
| 5,616,394 A | 4/1997 | Gorman et al. |
| 5,620,432 A * | 4/1997 | Goulait et al. ............... 604/390 |
| 5,624,427 A | 4/1997 | Bergman et al. |
| 5,624,429 A * | 4/1997 | Long et al. .................. 604/391 |
| 5,643,397 A | 7/1997 | Gorman et al. |
| 5,647,864 A | 7/1997 | Allen et al. |
| H1674 H | 8/1997 | Ames et al. |
| 5,655,843 A | 8/1997 | Conrad et al. |
| 5,669,897 A | 9/1997 | Lavon et al. |
| 5,669,900 A | 9/1997 | Bullwinkel et al. |
| 5,681,302 A | 10/1997 | Melbye et al. |
| 5,685,873 A | 11/1997 | Bruemmer |
| 5,722,969 A * | 3/1998 | Ito et al. ..................... 604/390 |
| 5,735,840 A | 4/1998 | Kline et al. |
| 5,749,866 A | 5/1998 | Roe et al. |
| 5,759,181 A | 6/1998 | Sayama et al. |
| 5,766,389 A | 6/1998 | Brandon et al. |
| 5,779,831 A | 7/1998 | Schmitz |
| 5,782,819 A | 7/1998 | Tanzer et al. |
| 5,785,699 A | 7/1998 | Schmitz |
| 5,795,350 A | 8/1998 | Schmitz |
| 5,814,178 A | 9/1998 | Jacobs |
| 5,830,206 A | 11/1998 | Larsson |
| 5,830,298 A | 11/1998 | Jackson |
| 5,843,068 A | 12/1998 | Allen et al. |
| 5,846,262 A | 12/1998 | Sayama et al. |
| 5,851,205 A * | 12/1998 | Hisada et al. ............... 604/390 |
| 5,853,405 A | 12/1998 | Suprise |
| 5,855,574 A | 1/1999 | Kling et al. |
| 5,876,394 A | 3/1999 | Rosch et al. |
| 5,879,500 A | 3/1999 | Herrin et al. |
| 5,888,607 A | 3/1999 | Seth et al. |
| 5,891,122 A | 4/1999 | Coates |
| 5,891,547 A | 4/1999 | Lawless |
| 5,897,545 A | 4/1999 | Kline et al. |
| 5,897,546 A * | 4/1999 | Kido et al. ................... 604/391 |
| 5,897,547 A | 4/1999 | Schmitz |
| 5,899,895 A | 5/1999 | Robles et al. |
| 5,906,008 A | 5/1999 | Heki et al. |
| 5,911,713 A | 6/1999 | Yamada et al. |
| 5,921,977 A | 7/1999 | Schmitz |
| 5,925,027 A | 7/1999 | Schmitz |

| | | | | | | | |
|---|---|---|---|---|---|---|---|
| 5,926,926 A | * | 7/1999 | Kato ............................ 604/391 | EP | 0 994 689 B1 | | 9/2002 |
| 5,928,212 A | | 7/1999 | Kline et al. | FR | 1375254 | | 9/1963 |
| 5,957,908 A | | 9/1999 | Kline et al. | GB | 1 520 740 | | 8/1978 |
| 5,967,665 A | | 10/1999 | MacDonald et al. | GB | 2 267 024 | A | 11/1993 |
| 5,968,031 A | | 10/1999 | Schmitz | GB | 2 303 045 | A | 2/1997 |
| 5,997,521 A | | 12/1999 | Robles et al. | GB | 2 315 402 | A | 2/1998 |
| 5,997,981 A | | 12/1999 | McCormack et al. | JP | 5-84322 | U | 11/1993 |
| 6,009,558 A | | 1/2000 | Rosch et al. | JP | 6-30962 | A | 2/1994 |
| 6,022,430 A | | 2/2000 | Blenke et al. | JP | 06-55623 | U | 8/1994 |
| 6,027,485 A | | 2/2000 | Matsushita et al. | JP | 6-55623 | U | 8/1994 |
| 6,030,373 A | * | 2/2000 | VanGompel et al. ........ 604/386 | JP | 6-285113 | A | 10/1994 |
| 6,063,466 A | * | 5/2000 | Tuschy et al. .............. 604/389 | JP | 9-66071 | A | 3/1997 |
| 6,086,571 A | | 7/2000 | Guevara et al. | JP | 9-187477 | A | 7/1997 |
| 6,099,516 A | * | 8/2000 | Pozniak et al. ............. 604/386 | JP | 11-99178 | A | 4/1999 |
| 6,113,717 A | | 9/2000 | Vogt et al. | WO | WO 93/17648 | A1 | 9/1993 |
| 6,115,847 A | | 9/2000 | Rosch et al. | WO | WO 95/02383 | A1 | 1/1995 |
| 6,146,738 A | | 11/2000 | Tsuji et al. | WO | WO 95/18589 | A1 | 7/1995 |
| D437,932 S | | 2/2001 | Ruman et al. | WO | WO 95/27460 | A1 | 10/1995 |
| D437,933 S | | 2/2001 | Fletcher et al. | WO | WO 95/27461 | A1 | 10/1995 |
| 6,192,521 B1 | | 2/2001 | Alberts et al. | WO | WO 95/27462 | A1 | 10/1995 |
| D438,614 S | | 3/2001 | Ratliff et al. | WO | WO 95/27463 | A1 | 10/1995 |
| D439,662 S | | 3/2001 | Ratliff et al. | WO | WO 95/29657 | A1 | 11/1995 |
| 6,210,388 B1 | | 4/2001 | Widlund et al. | WO | WO 96/19960 | A1 | 7/1996 |
| 6,213,991 B1 | | 4/2001 | Kling et al. | WO | WO 96/41604 | A1 | 12/1996 |
| 6,230,374 B1 | | 5/2001 | Widlund | WO | WO 97/04729 | A1 | 2/1997 |
| 6,264,643 B1 | | 7/2001 | Toyoda | WO | WO 97/23180 | A1 | 7/1997 |
| 6,287,287 B1 | | 9/2001 | Elsberg | WO | WO 97/36566 | A1 | 10/1997 |
| 6,302,871 B1 | | 10/2001 | Nakao et al. | WO | WO 97/46197 | A1 | 12/1997 |
| 6,328,725 B2 | | 12/2001 | Fernfors | WO | WO 97/48359 | A1 | 12/1997 |
| 6,329,016 B1 | | 12/2001 | Shepard et al. | WO | WO 98/18421 | A1 | 5/1998 |
| 6,332,250 B1 | | 12/2001 | Igaue et al. | WO | WO 98/18422 | A1 | 5/1998 |
| 6,352,528 B1 | | 3/2002 | Weber et al. | WO | WO 99/53881 | A1 | 10/1999 |
| 6,447,497 B1 | | 9/2002 | Olson | WO | WO 99/65441 | A1 | 12/1999 |
| 6,454,751 B1 | | 9/2002 | Olson | WO | WO 00/15069 | A1 | 3/2000 |
| 6,461,344 B1 | | 10/2002 | Widlund et al. | WO | WO 00/19950 | A1 | 4/2000 |
| 6,575,953 B2 | | 6/2003 | Olson | WO | WO 00/19951 | A1 | 4/2000 |
| 2002/0095131 A1 | | 7/2002 | Olson | WO | WO 00/20206 | A1 | 4/2000 |
| 2002/0099353 A1 | | 7/2002 | Olson | WO | WO 00/20207 | A1 | 4/2000 |

FOREIGN PATENT DOCUMENTS

| | | | |
|---|---|---|---|
| EP | 0 756 855 A1 | 2/1997 |
| EP | 0 812 584 A2 | 12/1997 |
| EP | 0 878 180 A2 | 11/1998 |
| EP | 0 757 550 B1 | 12/1998 |
| EP | 0 945 110 A2 | 9/1999 |
| EP | 0 641 552 B1 | 12/1999 |
| EP | 0 755 239 B1 | 12/1999 |
| EP | 0 800 379 B1 | 12/1999 |
| EP | 0 719 534 B1 | 4/2000 |
| EP | 0 721 769 B1 | 5/2000 |
| EP | 0 721 770 B1 | 5/2000 |
| EP | 0 547 497 B2 | 7/2000 |
| EP | 0 765 148 B1 | 11/2000 |
| EP | 0 951 266 B1 | 3/2002 |

| | | | |
|---|---|---|---|
| WO | WO 00/23025 A1 | 4/2000 |
| WO | WO 00/27236 A1 | 5/2000 |
| WO | WO 00/27328 A1 | 5/2000 |
| WO | WO 00/27329 A1 | 5/2000 |
| WO | WO 00/30581 A1 | 6/2000 |
| WO | WO 00/30584 A1 | 6/2000 |
| WO | WO 00/35395 A2 | 6/2000 |
| WO | WO 00/35396 A1 | 6/2000 |
| WO | WO 00/35397 A1 | 6/2000 |
| WO | WO 00/35398 A1 | 6/2000 |
| WO | WO 00/35399 A1 | 6/2000 |
| WO | WO 00/37009 A2 | 6/2000 |
| WO | WO 00/37016 A1 | 6/2000 |
| WO | WO 00/74621 A1 | 12/2000 |
| WO | WO 01/88245 A2 | 11/2001 |

* cited by examiner ved to be a
ABSORBENT ARTICLES HAVING DIFFERENTIAL STRENGTH REFASTENABLE SEAM This application claims the benefit of Provisional Application Ser. No. 60/112,709, filed Dec. 18, 1998.

BACKGROUND OF THE INVENTION

The present invention relates to absorbent articles which are adapted to contain body exudates. More particularly, the invention pertains to pant-like disposable absorbent articles having a refastenable, variable-location seam with differential strength properties, and methods of making such disposable absorbent articles.

Current disposable absorbent training pants for children going through the potty training stage have proved to be a particularly desirable and useful product. Such training pants generally include an absorbent chassis including a liquid impervious outer cover, a liquid pervious bodyside liner and an absorbent structure. The training pants further include elastic side panels that are permanently bonded to opposite side edges of the absorbent chassis. The chassis and side panels thereby form a unitary waist opening and two leg openings. The fit of the pants may be further enhanced by gathering means along the waist and leg openings.

The components of traditional training pants are permanently seamed together to provide a very durable pant product. Durability is a particularly significant quality for training pants, because the pants are typically worn by children of ages ranging from 20 to 48 months. Children in this age range are generally much more active and mobile than younger babies that wear diapers. Consequently, this level of activity and mobility mean that the training pants must withstand a significant degree of strain during use.

One drawback with current training pants, however, is that the manner of applying them is limited to being pulled on like a pant. Applying the product like a pant is advantageous in many instances, and is particularly suited for active, walking children. Even for the same child, however, there may be times when it would be useful to apply the product like a diaper. For instance, it might be more convenient to apply the product like a diaper when there is a desire not to remove the child's shoes. Because it is difficult to know when a particular mode of applying the garment will be needed, it is beneficial to have a garment that is adaptable to being used either as a diaper or as a pant. This is preferable to keeping both types of garments available. A product that can be applied either like a diaper or a pant permits the interior of the product to be easily checked without having to pull the product downward.

Thus, it would be desirable to have a disposable absorbent article that provides the durability of current training pants yet affords the option of being applied either like a diaper or like a pant.

SUMMARY OF THE INVENTION

In response to the above-referenced unfulfilled need in the prior art, a new disposable absorbent article and a method of making a disposable absorbent article have been discovered. The absorbent article includes a fastening system that can be repeatedly fastened, unfastened and refastened. The fastening system employs fasteners forming a refastenable, variable-location seam with differential strength properties to allow the fastener to be easily disengaged and to withstand relatively high separation forces that tend to occur at selected portions of the refastenable seam.

In one embodiment, the present invention pertains to an absorbent article that defines a longitudinal axis, a transverse axis, first and second longitudinally spaced waist regions, and a crotch region which extends between and interconnects the waist regions. The absorbent article includes an absorbent chassis and a fastening system for securing the absorbent article about the wearer. The fastening system includes at least one first fastening component attached to the absorbent chassis and disposed in the first waist region and at least one second fastening component attached to the absorbent chassis and disposed in the second waist region. The first and second fastening components together define a refastenable, variable-location seam having a main refastenable attachment zone providing a basic level of securement and an enhanced refastenable attachment zone providing an augmented level of securement. To provide selected regions with reinforced fastening, the augmented level of securement is greater than the basic level of securement.

The first and second fastening components form a refastenable, variable-location seam for securing the first and second waist regions together. The refastenable seam allows the product to be either pulled on like a pant or applied like a diaper. If the training pant becomes soiled during use, the first fastening components can be disengaged from the second fastening components to easily remove the training pant from the waist of the wearer with reduced risk of undesirably soiling the clothes or legs of the wearer. Further, the fastening components can also be easily disengaged from one another to inspect the training pant for possible soiling. Thus, the training pant is configured to be pulled on or off over the hips of the wearer such as conventional training pants and can be readily applied or removed by disengaging the fasteners similar to conventional diapers. The term "variable-location" is used herein to describe a seam formed by refastenable components that can be engaged with one another at an infinite number of attachment points, in contrast to cooperating fixed-point fasteners that engage one another at a finite number of positions. Suitable fastening components for forming a refastenable, variable-location seam include hook-and-loop materials, adhesives including cohesives, or the like. By comparison, examples of fixed-point fasteners include buckles, snaps, hook-and-eye components, zippers, buttons, clasps, or the like. Because they are variable-location fasteners, the first and second fastening components can be easily repositioned if necessary after the training pant has been pulled on over the legs and hips of the wearer.

The refastenable seam is designed to withstand considerable stresses during use. In particular, it has been discovered that the forces tending to disengage the fasteners during use are not uniformly distributed over the refastenable seam. Rather, these separation forces tend to be concentrated at identifiable points along the refastenable seam. The disclosed fastening components have been specifically constructed to provide differential levels of securement. The portions or zones of the refastenable seam that provide the greater levels of securement can be located at the points along the refastenable seam that are likely to experience the higher concentrations of separation forces.

In particular embodiments, for example, the refastenable seam has a waist opening end disposed toward the waist opening of the pant and an opposite leg opening end disposed toward one of the leg openings, and the enhanced refastenable attachment zone is disposed more toward the leg opening end. It has been recognized that higher concentrations of separation forces may tend to occur at the intersection of the refastenable seam and the leg openings.

This is believed to occur, especially with children of toilet training age, because the maximum circumference of the body is where the quadriceps insert into the hips. In this area, the absorbent article is under maximum stress and strain for two reasons. First, the maximum circumference puts the highest level of tension force into the transverse elastic components, such as elastic side panels, in this area of the pant. Second, the articulation of the leg also occurs in this area generating bending and compression forces in this area. This high tension and localized movement makes the lower portion of the refastenable seam prone to popping open. By selectively locating an enhanced refastenable attachment zone near the leg opening end of the refastenable seam, the greater levels of securement are positioned to coincide with the greater separation forces.

In other embodiments, the refastenable seam includes an enhanced refastenable attachment zone that is disposed toward the waist opening end of the refastenable seam. This particular orientation recognizes the fact that higher concentrations of separation forces may also occur at the intersection of the refastenable seam and the waist opening. Separation forces in this area may be attributable to pulling the pants over the hips, manually opening the waistband, or the like. Additionally, the refastenable seam may include a pair of enhanced refastenable attachment zones that are disposed toward the opposite waist opening and leg opening ends of the refastenable seam with the main refastenable attachment zone positioned between the enhanced refastenable attachment zones.

The refastenable seams are formed when the first and second fastening components are engaged with one another. The waist opening and leg opening ends of the refastenable seam are considered to be the most remote regions of the seam, toward the waist opening or leg openings of the pant, respectively, where the first and second fastening components releasably engage one another.

The refastenable seams are desirably relatively thin, narrow and flexible to afford the look and feel of a cloth garment. Thus, in particular embodiments, the refastenable seams have a length-to-width ratio of about 2 or greater, such as about 2 to about 25, particularly about 5 or greater, such as about 5 to about 8. The refastenable seams define a length dimension and a width dimension that is perpendicular to the length dimension. For a child of about 9 to about 15 kilograms (20–34 lbs.), for example, the length dimension is desirably from about 5 to about 13 centimeters, such as about 10 centimeters, and the width dimension is desirably from about 0.5 to about 3 centimeters, such as about 2 centimeters. Desirably although not necessarily, the length dimension can be aligned generally parallel to the longitudinal axis of the absorbent article and the width dimension can be aligned generally parallel to the transverse axis of the absorbent article. The term "generally parallel" as used herein refers to an angle within about 35 degrees or less of the referenced axis, and more particularly within about 20 degrees or less of the referenced axis.

The refastenable seam can include one or a plurality of main refastenable attachment zones and one or a plurality of enhanced refastenable attachment zones. While the enhanced refastenable attachment zones can be present anywhere along the length of the refastenable seam, they are desirably located along the length of the refastenable seam where there is likely to be a concentration of separation forces. As referenced above, one such area is toward the leg opening end of the refastenable seam. More specifically, the refastenable seam desirably comprises an enhanced refastenable attachment zone located at least partially within about 3 centimeters, particularly within about 2 centimeters, and more particularly within about 0.5 centimeter, of the leg opening end of the refastenable seam. Also as referenced above, another such area is toward the waist opening end of the refastenable seam. Thus, the refastenable seam desirably comprises an enhanced refastenable attachment zone located at least partially within about 5 centimeters, particularly within about 2.5 centimeters, and more particularly within about 0.5 centimeter, of the waist opening end of the refastenable seam.

A main refastenable attachment zone is desirably positioned in a central portion of the refastenable seam, intermediate the waist opening and leg opening ends. The main refastenable attachment zone or zones desirably comprise, cumulatively, about 95 percent or less of the length dimension of the refastenable seam, such as from about 20 to about 95 percent of the length dimension, and particularly from about 80 to about 90 percent of the length dimension. Correspondingly, the enhanced refastenable attachment zone or zones desirably comprise, cumulatively, about 80 percent or less of the length dimension of the refastenable seam, such as from about 5 to about 80 percent of the length dimension, and particularly from about 10 to about 20 percent of the length dimension.

Even though enhanced refastenable attachment zones are used to prevent unexpected disengagement of the fastening components, the fastening components are designed to be relatively easy to disengage from one another. In particular, the main refastenable attachment zone is suitably designed to provide a basic level of securement that allows the first and second fastening components to begin to disengage from one another without undue force. The refastenable seam would be more difficult to disengage, in fact needlessly difficult to disengage, if the entire refastenable seam were provided with a single level of securement that was targeted to withstand the greatest separation force that was likely to be experienced at any point along the length of the refastenable seam.

Hence, in particular embodiments, the basic level of securement can be from about 30 grams to about 1000 grams, and particularly from about 40 to about 750 grams. The augmented level of securement is greater than the basic level of securement, for example by about 125 percent or more, particularly by about 200 percent or more, and more particularly by about 300 percent or more. In particular embodiments, the enhanced level of securement can be from about 65 grams to about 4000 grams, and particularly from about 150 to about 1500.

The level of securement of any particular area of the refastenable seam can be quantified using the following Peel Test method, which is designed to quantify, in grams, the peak and the average dynamic peel strength of the refastenable seam holding the front waist region of the absorbent article to the rear waist region. The direction of force in this application is generally perpendicular to the longitudinal centerline of the product.

Sample Preparation

The size of suitable samples of refastenable seam material having a single enhanced refastenable attachment zone can measure 7.6 cm. by 1.9 cm. (3 by 0.75 inch), with the enhanced refastenable attachment zone located 0.6 cm. (0.25 inch) inboard of one end edge. The size of the sample may need to be adjusted for different refastenable seam configurations.

Equipment

1. Constant rate of extension tensile tester equipped with an appropriate load cell. A suitable tensile testing system is a Sintech Tensile Tester, commercially available from MTS, Research Triangle Park, N.C., under the trade designation Sintech Model 1/G Tensile Tester.

2. Software commercially obtained from MTS under the trade designation MTS TESTWORKS® for Windows Version 3.10.

3. Pneumatic-action grips commercially available from Instron Corporation, Canton, Mass., under the trade designation Instron Model 2712-004.

4. 2.5 cm. by 10.1 cm. (1 by 4 inch) grip faces, rubber coated, commercially available from Instron Corporation, Canton, Mass.

5. Test facility having a temperature of 23±1° C., and a relative humidity of 50±2 percent.

Test Procedure

1. A sample to be tested is conditioned in the test facility for at least 4 hours prior to testing.

2. A 2041.2 grams (4.5 lb.) roller with a total diameter of 95 mm., the outer 6.7 mm. of which is rubber, is rolled over the sample from one end to the other and then back again (1 cycle).

3. The load cell is calibrated and the software loaded.

4. The grips are installed on the tensile tester with the jaws closed.

5. The test conditions for the tensile tester are set as follows:

Crosshead speed: 500 millimeters/minute

Full-scale load: 11.34 kilograms (25 lbs.)

Gage length: 25.4 millimeters (1 inch)

6. The weight of the clamp is tared out.

7. The sample is pulled apart on the end opposite from the enhanced refastenable attachment zone so that the fastening component and the mating fastening component disengage to form free ends each 25.4 millimeters long.

8. The free end of the fastening component on the back waist region of the article is inserted into the upper jaw.

9. The free end of the mating fastening component on the front waist region of the article is inserted into the lower jaw, such that the fastened inner surface of the back waist region and the fastened inner surface of the front waist region are facing the same direction and are parallel to one another. The lower jaw is closed.

10. The crosshead is started in motion, and the test is run until the fastening component and mating fastening component are no longer connected.

11. The average load needed to separate the fastener is recorded for the main refastenable attachment zone by averaging load values at separation distances that avoid the enhanced refastenable attachment zone, for example from 1 cm. by 6.4 cm. (0.4 to 2.5 inch) for the sample specified in the Sample Preparation section above. The peak load needed to separate the fastening components is recorded for the enhanced refastenable attachment zone(s). Two or more tests may be needed to obtain values for the main and enhanced refastenable attachment zones.

The ease of disengaging the fastening components may be improved by positioning the enhanced refastenable attachment zone or zones inward from the edges of the refastenable seam. Desirably, a main refastenable attachment zone, that is a zone of the refastenable seam having a basic level of securement, is disposed between the enhanced refastenable attachment zone and the side edges of the refastenable seam. With this positioning, the portion of the main refastenable attachment zone that is positioned transversely outward from the enhanced refastenable attachment zone would function as a type of finger tab to facilitate easier opening of the seam. In particular embodiments, the enhanced refastenable attachment zone or zones can be positioned inward from the side edges of the refastenable seam, and particularly the side edges of the refastenable seam that is nearest the corresponding side edge of the absorbent article, and at least one main refastenable attachment zone disposed between the side edges of the refastenable seam and the enhanced refastenable attachment zone or zones.

The fastening components can comprise any refastenable fasteners suitable for forming a variable-location seam in absorbent articles, such as mechanical fastening elements or adhesive fastening elements. Suitable mechanical fastening elements may be provided by interlocking geometric shaped materials, such as hooks, loops, bulbs, mushrooms, arrowheads, balls on stems, male and female mating components, or the like. In particular embodiments, the first and second components comprise hook-and-loop fastening elements.

The main and enhanced refastenable attachment zones can be constructed using a variety of techniques to provide the differential levels of securement. For instance, a single type of fastening component may be employed for the main refastenable attachment zones, and a combination of two or more types of fastening components that work in concert may be employed for the enhanced refastenable attachment zones. Alternatively, one type of fastening component may be employed for the main refastenable attachment zones, and a different, more aggressive type of fastening component may be used for the enhanced refastenable attachment zones.

In one embodiment, one of the first or second fastening components comprises at least one primary region and at least one secondary region, where the primary and secondary regions have different releasable engagement properties. For purposes of the present invention, the phrase "different releasable engagement properties" is used to mean different levels of securement as measured by the Peel Test procedure set forth above. The primary region comprises a mechanical fastening component, such as hook material, and the secondary region comprises an adhesive disposed on and working in concert with a mechanical fastening component. The adhesive can be pulsed onto the hook material in localized regions to reinforce the engagement of the interlocking geometric shaped materials in those regions. The adhesive used in such embodiments desirably remains tacky so that it continues to reinforce the seam in that region after multiple engagement and disengagement cycles. Adhesives suitable for forming such an enhanced refastenable attachment zone are described generally as construction adhesives, and are available from various adhesive suppliers such as National Starch, Bridgewater, N.J., U.S.A. In one particular embodiment, the adhesive comprises an SBS block copolymer having a modulus of about $10^9$ to $10^{10}$ and a shear rate of 10 radians/sec, an example of which is identified as National Starch No. 345610 or 5610. The adhesive can be applied at an add-on level of about 1 gram per square centimeter or less, and particularly about 0.5 gram per square centimeter or less, such as about 0.01 to about 0.25 grams per square centimeter. The desired reinforcing and re-attachment properties are achieved by balancing the modulus, tack and add-on of the adhesive. In this embodiment, the primary region forms the main refastenable attachment zone of the refastenable seam and the secondary region forms the enhanced refastenable attachment zone of the refastenable seam.

Hence, in another embodiment, the present invention pertains to an absorbent article including an absorbent chassis and a fastening system. The fastening system includes at least one first fastening component attached to the absorbent chassis and disposed in the first waist region and at least one second fastening component attached to the absorbent chassis and disposed in the second waist region. The first and second fastening components include mechanical fastening elements having a plurality of upwardly extending engaging elements and also include an adhesive disposed on at least some of the upwardly extending engaging elements. The first and second fastening components together define a refastenable, variable-location seam having a main refastenable attachment zone providing a basic level of securement and an enhanced refastenable attachment zone providing an augmented level of securement, which is greater than the basic level of securement.

In alternative embodiments, the primary region or regions of the fastening component are constructed of a particular mechanical or adhesive fastening element, and the secondary regions of the fastening component are constructed of a more aggressive mechanical or adhesive fastening element. By way of illustration, the first fastening component can be constructed of two or more mechanical fastening elements having different properties that result in different levels of securement strength. The second fastening component can comprise a uniform mechanical fastening component, or may similarly comprise two or more mechanical fastening components. Using hook material as an illustrative example, one skilled in the art would recognize that the shape, density and polymer composition of the hooks may be selected to obtain the desired level of securement between the first and second fastening components. A more aggressive hook material may comprise a material with a greater average hook height, a greater percentage of directionally-aligned hooks, or a more aggressive hook shape.

Thus, where the first and second fastening components comprise hook-and-loop materials, the primary and secondary regions may comprise different types of hook materials or different types of loop materials, or may further comprise an adhesive material. Where the first and second fastening components comprise adhesive fasteners, the primary and secondary regions may comprise different types of adhesive materials. Either one or both of the first and second fastening component may comprise primary and secondary regions that have different releasable engagement properties.

Where separate fastener materials are used to form the different refastenable attachment zones, any spacing between the fastener materials should be kept to 2 centimeters or less, particularly 1 centimeter or less, and more particularly 0.5 centimeter or less. As disclosed in copending U.S. Patent Application Serial No. 60/112,775, filed on Dec. 18, 1998 by C. P. Olson and titled "Absorbent Articles Having Hinged Fasteners," such narrow spacings between fastener materials may provide a desirable hinge to improve fit and securement of the fastening components.

The disclosed absorbent articles are adapted to be worn adjacent to the body of a wearer to absorb and contain various exudates discharged from the body. The absorbent articles are desirably pre-fastened to provide a pant-like product for the user. The product can then be pulled on like a conventional training pant, and subsequently checked or removed with the ease of a diaper-like product. Moreover, the product may be applied like a diaper rather than like a pant. Supplemental releasable fastening means such as frangible point bonds may be employed to maintain the absorbent article in a pant configuration until the user intentionally disengages the fasteners.

The fastening system allows for easy inspection of the interior of the pant-like product. If necessary, the fastening system also allows the pant to be removed quickly and easily. This is particularly beneficial when the pant contains messy excrement. If desired, the caregiver can completely remove the pant-like product and replace it with a new one without having to remove the child's shoes and clothing. The present fastening system may be used with a wide variety of absorbent products, including training pants, diapers, incontinence garments, or other garments using mechanical or adhesive fasteners.

The present invention also pertains to a method of making an absorbent article. In one embodiment, a method of making an absorbent article comprises providing an absorbent chassis and attaching at least one first fastening component to the absorbent chassis in a first waist region and attaching at least one second fastening component to the absorbent chassis in a second waist region, wherein the first and second fastening components together define a refastenable, variable-location seam and the first fastening component comprises primary and secondary regions that have different releasable engagement properties.

In an alternative embodiment, a method of making an absorbent article comprises: providing an absorbent chassis; providing a first mechanical fastening component having a backing structure, an engagement surface, and a plurality of engaging elements extending upwardly from the engagement surface, the first mechanical fastening component defining a primary region and a secondary region; applying an adhesive to the engaging elements in the secondary region; maintaining the engaging elements in the primary region free of the adhesive; attaching the first mechanical fastening component to the absorbent chassis in the first waist region; and attaching at least one second mechanical fastening component to the absorbent chassis in the second waist region; wherein the first and second mechanical fastening components are adapted to releasably engage one another, and the primary and secondary regions have different releasable engagement properties.

Adhesive may be applied to the fastening components using a variety of techniques, such as spraying, printing, dipping, or the like. The strength of adhesion between the adhesive and the fastening components or the strength of cohesion between the cohesives can vary over a relatively wide range. In particular embodiments, the adhesive and/or cohesive remains tacky such that the adhesive and/or cohesive forms a refastenable bond. Stronger adhesives and/or cohesives can be applied onto the fastening components in a non-uniform and/or less concentrated pattern.

A more detailed description of the construction and design of one form of training pant can be found in U.S. Pat. No. 4,940,464 issued Jul. 10, 1990 to Van Gompel et al., which is incorporated herein by reference. The Van Gompel et al. patent describes various materials of which the training pant can be made, and a method of constructing a training pant.

DEFINITIONS

Within the context of this specification, each term or phrase below will include the following meaning or meanings.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Cohesive" describes a material or composition that is self-sticking in that it only adheres to itself.

"Comprising" is inclusive or open-ended and does not exclude additional, unrecited elements or method steps.

"Connected" refers to the joining, adhering, bonding, attaching, or the like, of two elements. Two elements will be considered to be connected together when they are connected directly to one another or indirectly to one another, such as when each is directly connected to intermediate elements.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Fabrics" is used to refer to all of the woven, knitted and nonwoven fibrous webs.

"Flexible" refers to materials which are compliant and which will readily conform to the general shape and contours of the wearer's body.

"Force" includes a physical influence exerted by one body on another which produces acceleration of bodies that are free to move and deformation of bodies that are not free to move. Force is expressed in grams per unit area.

"Graphic" refers to any design, pattern, or the like that is visible on an absorbent article.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° designated "nonwettable" or hydrophobic.

"Integral" is used to refer to various portions of a single unitary element rather than separate structures bonded to or placed with or placed near one another.

"Inward" and "outward" refer to positions relative to the center of an absorbent article, and particularly transversely and/or longitudinally closer to or away from the longitudinal and transverse center of the absorbent article.

"Layer" when used in the singular can have the dual meaning of a single element or a plurality of elements.

"Liquid impermeable", when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

"Longitudinal" and "transverse" have their customary meaning, as indicated by the longitudinal and transverse axes depicted in FIGS. 2 and 3. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Member" when used in the singular can have the dual meaning of a single element or a plurality of elements.

"Nonwoven web" means a web of material which is formed without the aid of a textile weaving or knitting process.

"Operatively joined," with reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Outer cover graphic" refers to a graphic that is directly visible upon inspection of the exterior surface of a garment, and for a refastenable garment is in reference to inspection of the exterior surface of the garment when the fastening system is engaged as it would be during use.

"Permanently bonded" refers to the joining, adhering, connecting, attaching, or the like, of two elements of an absorbent garment such that the elements tend to be and remain bonded during normal use conditions of the absorbent garment.

"Refastenable" refers to the property of two elements being capable of releasable attachment, separation, and subsequent releasable reattachment without substantial permanent deformation or rupture.

"Releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

"Rupture" means the breaking or tearing apart of a material; in tensile testing, the term refers to the total separation of a material into two parts either all at once or in stages, or the development of a hole in some materials.

"Stretch bonded" refers to an elastic member being bonded to another member while the elastic member is extended at least about 25 percent of its relaxed length. Desirably, the term "stretch bonded" refers to the situation wherein the elastic member is extended at least about 100 percent, and more desirably at least about 300 percent, of its relaxed length when it is bonded to the other member.

"Stretch bonded laminate" refers to a composite material having at least two layers in which one layer is a gatherable layer and the other layer is an elastic layer. The layers are joined together when the elastic layer is in an extended condition so that upon relaxing the layers, the gatherable layer is gathered.

"Surface" includes any layer, film, woven, nonwoven, laminate, composite, or the like, whether pervious or impervious to air, gas, and/or liquids.

"Tension" includes a uniaxial force tending to cause the extension of a body or the balancing force within that body resisting the extension.

"Thermoplastic" describes a material that softens when exposed to heat and which substantially returns to a non-softened condition when cooled to room temperature.

These terms may be defined with additional language in the remaining portions of the specification.

BRIEF DESCRIPTION OF THE DRAWINGS

The above-mentioned and other features of the present invention and the manner of attaining them will become more apparent, and the invention itself will be better understood by reference to the following description and the accompanying drawings, wherein similar features in different figures have been given the same reference numeral.

DETAILED DESCRIPTION OF THE DRAWINGS

The principles of the present invention can be incorporated into any suitable disposable absorbent article and its method of manufacture. Examples of such suitable articles include diapers, training pants, feminine hygiene products, incontinence products, other personal care or health care garments, or the like. For ease of explanation, the description hereafter will be in terms of a child's training pant.

Figure 1:
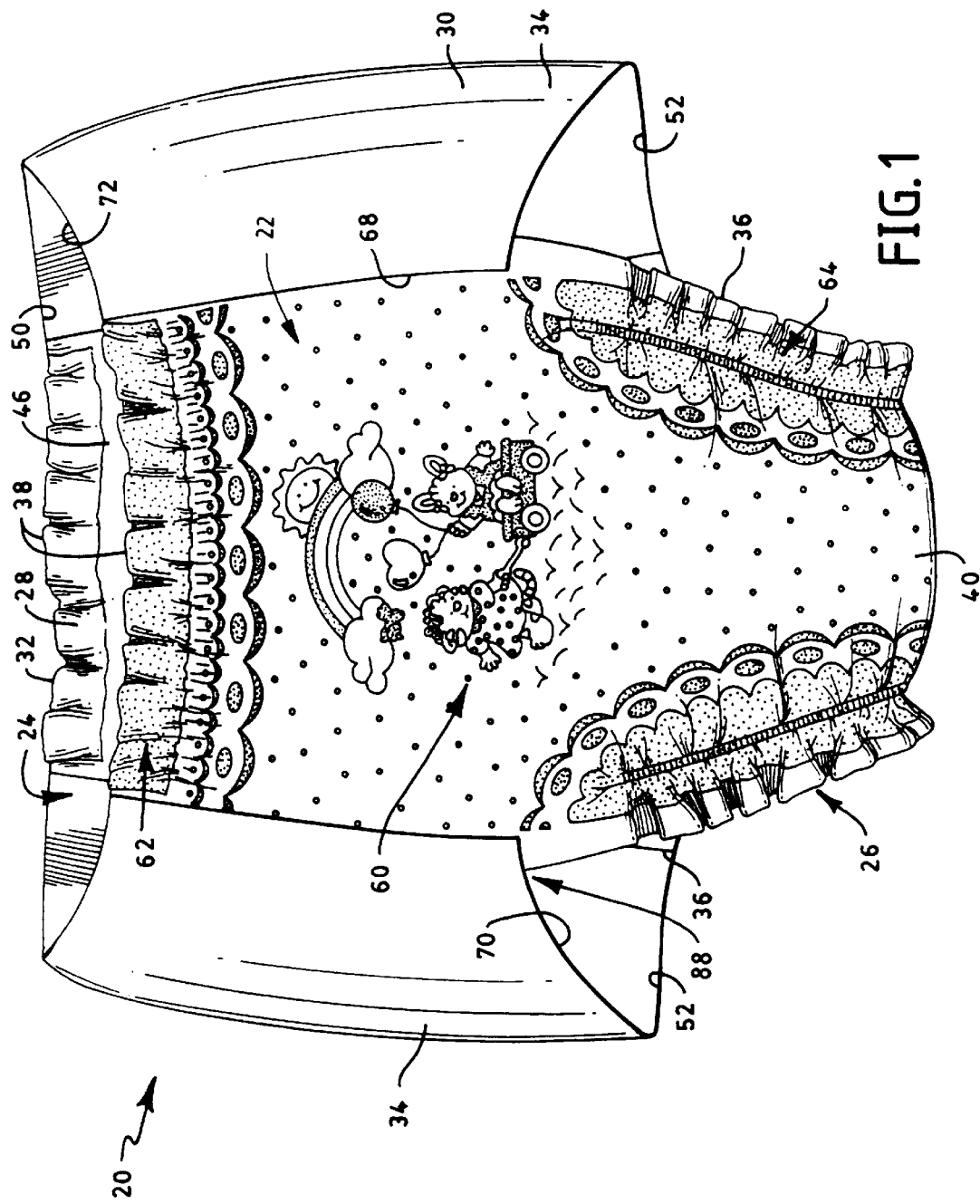
FIG. 1 illustrates a front perspective view of one type of disposable absorbent article incorporating the principles of the present invention.

With reference to FIG. 1, a disposable absorbent article, such as a training pant 20, is illustrated in a fastened condition as the product would be configured when worn. The training pant 20 comprises an absorbent chassis 32 and a fastening system 80. The absorbent chassis 32 defines a front waist region 22, a back waist region 24, a crotch region 26 interconnecting the front and back waist regions, an inner surface 28 which is configured to contact the wearer, and an outer surface 30 opposite the inner surface which is configured to contact the wearer's clothing. With additional reference to FIGS. 2 and 3, the absorbent chassis 32 also defines a pair of transversely opposed side edges 36 and a pair of longitudinally opposed waist edges 38. The front waist region 22 is contiguous with the front waist edge 38, and the back waist region 24 is contiguous with the back waist edge 39.

Figure 2:
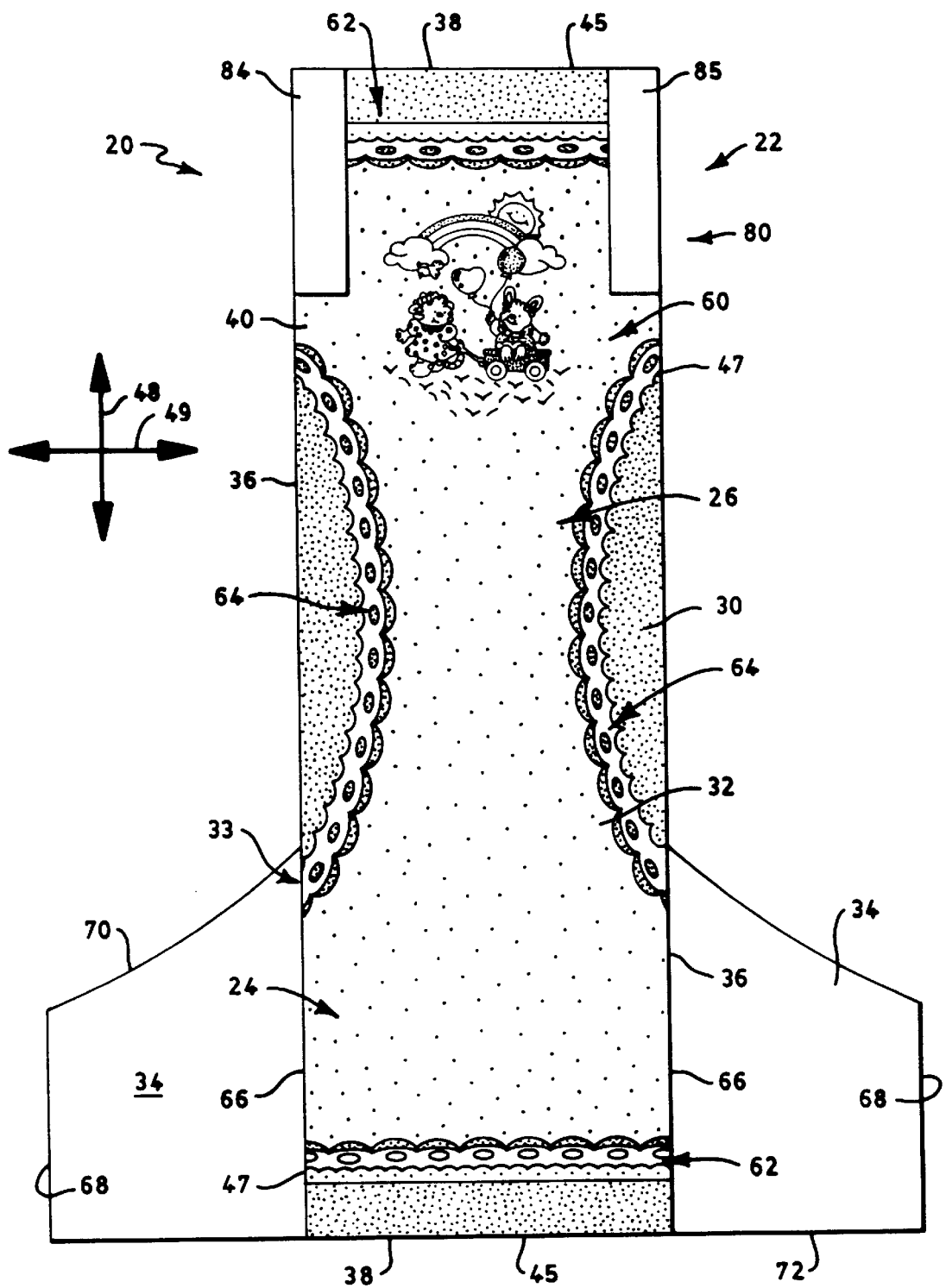
FIG. 2 illustrates a plan view of the disposable absorbent article shown in FIG. 1 in an unfastened, stretched and laid flat condition, and showing the surface of the article that faces away from the wearer.
Figure 3:
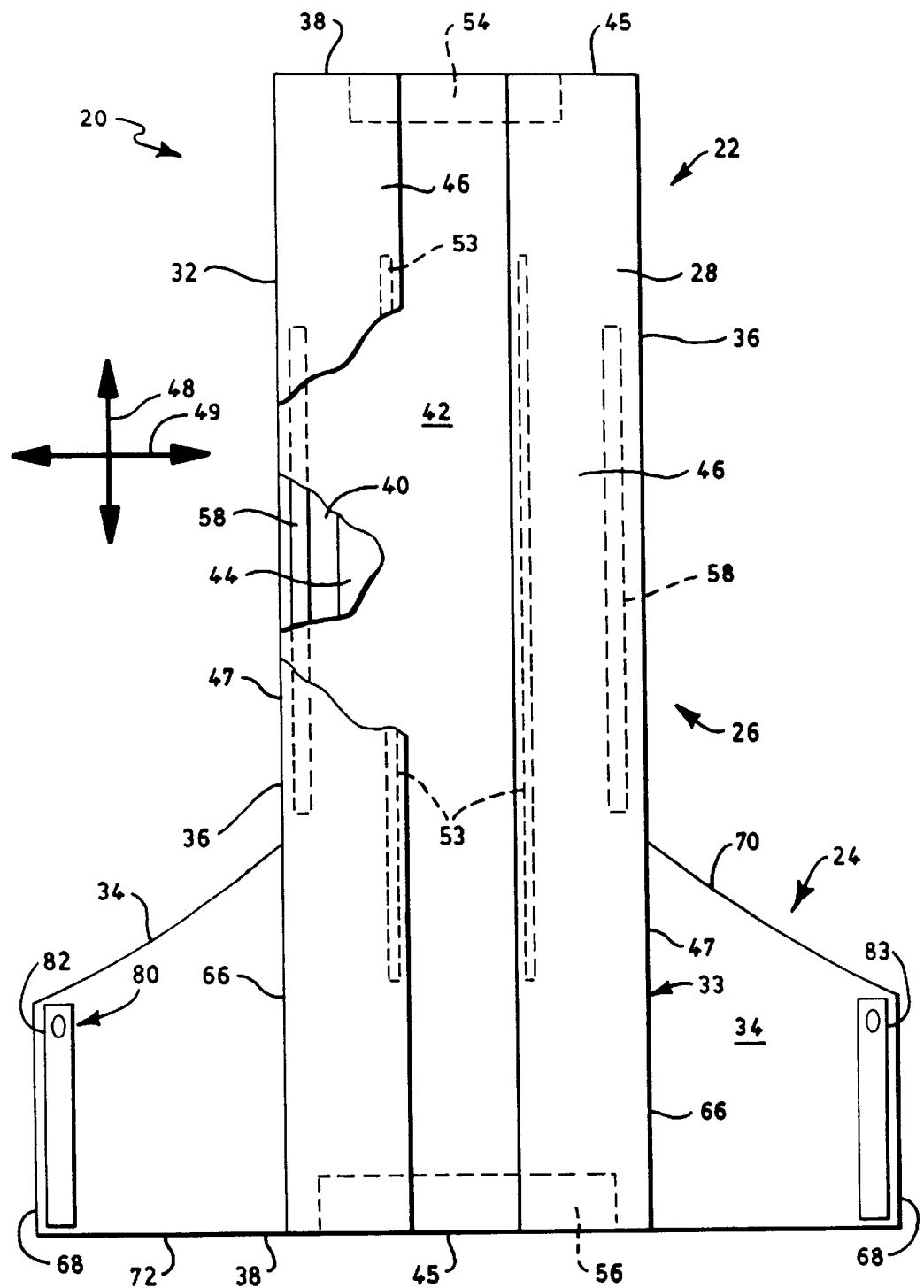
FIG. 3 illustrates a plan view similar to FIG. 2, but showing the surface of the article that faces the wearer when the article is worn, and with portions cut away to show the underlying features.

The illustrated absorbent chassis 32 comprises a generally rectangular composite structure 33 and a pair of transversely opposed side panels 34. The composite structure 33 and side panels 34 may be integrally formed or comprise two or more separate elements, as shown. The illustrated composite structure 33 comprises an outer cover 40, a bodyside liner 42 which is connected to the outer cover in a superposed relation, an absorbent assembly 44 (FIGS. 2 and 3 ) which is located between the outer cover and the bodyside liner, and a pair of containment flaps 46 (FIGS. 1 and 3). The rectangular composite structure 33 has opposite linear end edges 45 that form portions of the front and back waist edges 38, and opposite linear side edges 47 that form portions of the side edges 36 of the absorbent chassis 32 (FIGS. 2 and 3). For reference, arrows 48 and 49 depicting the orientation of the longitudinal axis and the transverse axis, respectively, of the training pant 20 are illustrated in FIGS. 2 and 3.

With the training pant 20 in the fastened position as illustrated in FIG. 1, the front and back waist regions 22 and 24 are joined together to define a three dimensional pant configuration having a waist opening 50 and a pair of leg openings 52. The front waist region 22 comprises the portion of the training pant 20 which, when worn, is positioned on the front of the wearer while the back waist region 24 comprises the portion of the training pant which, when worn, is positioned on the back of the wearer. The crotch region 26 of the training pant 20 comprises the portion of the training pant which, when worn, is positioned between the legs of the wearer and covers the lower torso of the wearer. The side panels 34 comprise the portions of the training pant 20 which, when worn, are positioned on the side hip regions of the wearer. The waist edges 38 of the absorbent chassis 32 of the training pant 20 and the side panels 34 are configured to encircle the waist of the wearer when worn and provide the waist opening 50 which defines a waist perimeter dimension. The transversely opposed side edges 36 of the absorbent chassis 32 and the side panels 34 of the training pant 20 generally define the leg openings 52.

The absorbent chassis 32 is configured to contain and/or absorb any body exudates discharged from the wearer. For example, the absorbent chassis 32 desirably although not necessarily comprises the pair of containment flaps 46 which are configured to provide a barrier to the transverse flow of body exudates. A flap elastic member 53 (FIG. 3) is operatively joined with each containment flap 46 in any suitable manner as is well known in the art. The elasticized containment flaps 46 define an unattached edge which assumes an upright, generally perpendicular configuration in at least the crotch region 26 of the training pant 20 to form a seal against the wearer's body. The containment flaps 46 can be located along the transversely opposed side edges of the absorbent chassis 32, and can extend longitudinally along the entire length of the absorbent chassis or may only extend partially along the length of the absorbent chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pant 20 desirably includes a front waist elastic member 54, a rear waist elastic member 56, and leg elastic members 58, as are known to those skilled in the art (FIG. 3). The waist elastic members 54 and 56 can be operatively joined to the outer cover 40 and/or bodyside liner 42 along the opposite waist edges 38, and can extend over part or all of the waist edges. The leg elastic members 58 are desirably operatively joined to the outer cover 40 and/or bodyside liner 42 along the opposite side edges 36 and positioned in the crotch region 26 of the training pant 20.

The flap elastic members 53, the waist elastics 54 and 56, and the leg elastics 58 can be formed of any suitable elastic material. As is well known to those skilled in the art, suitable elastic materials include sheets, strands or ribbons of natural rubber, synthetic rubber, or thermoplastic elastomeric polymers. The elastic materials may be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 58 comprise a plurality of dry-spun coalesced multifilament spandex elastomeric threads sold under the trade name LYCRA® and available from E. I. Du Pont de Nemours and Company, Wilmington, Del., U.S.A.

The outer cover 40 desirably comprises a material that is substantially liquid impermeable, and can be elastic, stretchable or nonstretchable. The outer cover 40 can be a single layer of liquid impermeable material, but desirably comprises a multi-layered laminate structure in which at least one of the layers is liquid impermeable. For instance, the outer cover 40 can include a liquid permeable outer layer and a liquid impermeable inner layer that are suitably joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wis., U.S.A. or from National Starch and Chemical Company, Bridgewater, N.J., U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable bodyside liner 42 is made. While it is not a necessity for the outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and caregiver. A suitable liquid impermeable film for use as liquid impermeable inner layer, or a single layer liquid impermeable outer cover 40, is a 1.0 mil polyethylene film commercially available from Edison Plastics Company of South Plainfield, N.J., U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn., U.S.A.

As shown in FIGS. 1 and 2, the training pant 20 and in particular the outer cover 40 desirably comprises one or more appearance-related components. Examples of appearance-related components include, but are not limited to, graphics; highlighting or emphasizing leg and waist openings in order to make product shaping more evident or visible to the user; highlighting or emphasizing areas of the product to simulate functional components such as elastic leg bands, elastic waistbands, simulated "fly openings" for boys, ruffles for girls; highlighting areas of the product to change the appearance of the size of the product; registering wetness indicators, temperature indicators, and the like in the product; registering a back label, or a front label, in the product; and registering written instructions at a desired location in the product.

The illustrated training pant 20, which is designed for use by young girls, includes a registered graphic 60. In this design, the registered graphic 60 includes simulated waist ruffles 62, simulated leg ruffles 64, a rainbow, sun, clouds, wagon and balloon. Again, any suitable design can be utilized for a training pant intended for use by young girls, so as to be aesthetically and/or functionally pleasing to them and the caregiver. The appearance-related components are desirably positioned on the training pant 20 at selected locations, which can be carried out using the methods disclosed in U.S. Pat. No. 5,766,389 issued Jun. 16, 1998 to Brandon et al., which is incorporated herein by reference.

The liquid permeable bodyside liner 42 is illustrated as overlying the outer cover 40 and absorbent assembly 44, and may but need not have the same dimensions as the outer cover 40. The bodyside liner 42 is desirably compliant, soft feeling, and non-irritating to the child's skin. Further, the bodyside liner 42 can be less hydrophilic than the absorbent assembly 44, to present a relatively dry surface to the wearer and permit liquid to readily penetrate through its thickness.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.28 weight percent of a surfactant commercially available from the Rohm and Haas Co. under the trade designation Triton X-102. The surfactant can be applied by any conventional means, such as spraying, printing, brush coating or the like. The surfactant can be applied to the entire bodyside liner 42 or may be selectively applied to particular sections of the bodyside liner, such as the medial section along the longitudinal centerline.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like.

The absorbent assembly 44 (FIG. 3) is positioned between the outer cover 40 and the bodyside liner 42, which components can be joined together by any suitable means such as adhesives as is well known in the art. The absorbent assembly 44 can be any structure which is generally compressible, conformable, non-irritating to the child's skin, and capable of absorbing and retaining liquids and certain body wastes. The absorbent assembly 44 can be manufactured in a wide variety of sizes and shapes, and from a wide variety of liquid absorbent materials commonly used in the art. For example, the absorbent assembly 44 can suitably comprise a matrix of hydrophilic fibers, such as a web of cellulosic fluff, mixed with particles of a high-absorbency material commonly known as superabsorbent material. In a particular embodiment, the absorbent assembly 44 comprises a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or may be nonuniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can comprise a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A. and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 44 is generally rectangular in shape, and comprises a blend of wood pulp fluff and superabsorbent material. One preferred type of fluff is identified with the trade designation CR1654, available from Kimberly-Clark Corporation, Neenah, Wis., U.S.A. and is a bleached, highly absorbent sulfate wood pulp containing primarily soft wood fibers. As a general rule, the superabsorbent material is present in the absorbent assembly 44 in an amount of from about 5 to about 90 weight percent based on total weight of the absorbent assembly. The absorbent assembly 44 suitably has a density within the range of about 0.10 to about 0.35 grams per cubic centimeter. The absorbent assembly 44 may or may not be wrapped or encompassed by a suitable tissue wrap that maintains the integrity and/or shape of absorbent assembly.

The absorbent chassis 32 can also incorporate other materials that are designed primarily to receive, temporarily store, and/or transport liquid along the mutually facing surface with absorbent assembly 44, thereby maximizing the absorbent capacity of absorbent assembly. One suitable material is referred to as a surge layer (not shown) and comprises a material having a basis weight of about 50 grams per square meter, and comprising a through-air-bonded-carded web of a homogenous blend of 60 percent 3 denier bicomponent fiber comprising a polyester core/polyethylene sheath, commercially available from BASF Corporation, and 40 percent 6 denier polyester fiber, commercially available from Hoechst Celanese Corporation, Portsmouth, Va., U.S.A.

As noted previously, the illustrated training pant 20 has a side panel 34 disposed on each side of the absorbent chassis 32. The pair of transversely opposed side panels 34 are permanently bonded to the composite structure 33 of the absorbent chassis 32 in at least one of the waist regions 22 and 24 and releasably attached to the absorbent chassis in the opposite waist region. For example, as shown best in FIGS. 2 and 3, the side panels 34 are permanently bonded to and extend transversely beyond the side edges 47 of the composite structure 33 in the back waist region 24 along an attachment line 66. It is desirable but not necessary for the side panels 34 to extend transversely outward from the composite structure.

The illustrated side panels 34 define a distal edge 68 spaced from the attachment line 66 and inner and outer edges 70 and 72 that extend from the side edges 36 of the absorbent chassis 32 to the distal edges. The inner edges 70 of the side panels 34 form part of the side edges 36 of the absorbent chassis 32 and are desirably although not necessarily angled relative to the transverse axis 49 to provide greater coverage toward the back of the pant as compared to the front of the pant. The outer edges 72 are desirably parallel to the transverse axis 49 and form part of the back waist edge 38 of the absorbent chassis 32. Further, the outer edges 72 are desirably substantially aligned with the linear end edges 45 of the composite structure 33, and particularly longitudinally offset by about 1 centimeter or less.

In particular embodiments for improved fit and appearance, the side panels 34 desirably have an average length dimension measured parallel to the longitudinal axis 48 that is about 20 percent or greater, and particularly about 25 percent or greater, of the overall length dimension of the absorbent article, also measured parallel to the longitudinal axis 48. For example, in training pants having an overall length dimension of about 54 centimeters, the side panels 34 desirably have an average length dimension of about 10 centimeters or greater, such as about 15 centimeters. As illustrated the side panels 34 extend from the waist opening 50 to one of the leg openings 52 and have a continually decreasing length dimension moving from the attachment line 66 to the distal edge 68.

The side panels 34 are permanently bonded to the composite structure 33 along the attachment line 66 using attachment means known to those skilled in the art such as adhesive, thermal or ultrasonic bonding. In such a configuration, each of the side panels 34 can be releasably attached to the composite structure 33 in the front waist region 22 of the training pant 20 as will be discussed hereinafter in more detail. Alternatively, the side panels 34 may be permanently bonded to the side edges 47 in the front waist region 22 and releasably attached to the side edges 36 in the back waist region 24 if it is desired that the fasteners be located towards the back of the wearer. Such a configuration may be desirable to prevent a wearer from unfastening the article prematurely. The side panels can also be formed as a portion of a component of the composite structure 33, such as the outer cover or the bodyside liner.

Each of the side panels 34 can include one or more individual, distinct pieces of material. In particular embodiments, for example, each side panel 34 can include front and back side panel portions that are joined at a seam (not shown). Still alternatively, each individual side panel 34 can include a single piece of material which is folded over upon itself along an intermediate fold line (not shown). In other embodiments, both the front and back waist regions include side panels (not shown).

The side panels 34 desirably comprise an elastic material capable of stretching in a direction parallel to the transverse axis 49 of the training pant 20. Suitable elastic materials, as well as one described process of incorporating elastic side panels into a training pant, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material comprises a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Mormon; and European Patent Application No. EP 0 217 032 published on Apr. 8, 1987 in the names of Taylor et al.; all of which are incorporated herein by reference. Alternatively, the side panel material may comprise other woven or nonwoven materials, such as those described above as being suitable for the outer cover 40 or bodyside liner 42.

The training pant 20 according to the present invention also includes a fastening system 80 for securing the training pant about the waist of the wearer (FIGS. 2 and 3). The illustrated fastening system 80 includes a pair of first fastening components 82 and 83 that are adapted to refastenably connect to a pair of second fastening components 84 and 85. In one embodiment, one surface of each of the first fastening components 82 and 83 comprises a plurality of engaging elements that project from that surface. The engaging elements of these fastening components 82 and 83 are adapted to repeatedly engage and disengage the engaging elements of the other fastening components 84 and 85.

In one particular embodiment, the first fastening components 82 and 83 each comprise hook type fasteners and the second fastening components 84 and 85 each comprise complementary loop type fasteners. In another particular embodiment, the first fastening components 82 and 83 each comprise loop type fasteners and the second fastening components 84 and 85 each comprise complementary hook type fasteners. Loop type fasteners typically comprise a fabric or material having a base or backing structure and a plurality of loop members extending upwardly from at least one surface of the backing structure. The loop material can be formed of any suitable material, such as acrylic, nylon or polyester, and can be formed by methods such as warp knitting, stitch bonding or needle punching. Suitable loop materials are available from Guilford Mills, Inc., Greensboro, N.C., U.S.A. under the trade designation No. 36549.

Hook type fasteners typically comprise a fabric or material having a base or backing structure and a plurality of hook members extending upwardly from at least one surface of the backing structure. In contrast to the loop type fasteners which desirably comprise a flexible fabric, the hook material advantageously comprises a resilient material to minimize unintentional disengagement of the fastener components as a result of the hook material becoming deformed and catching on clothing or other items. The term "resilient" as used herein refers to an interlocking material having a predetermined shape and the property of the interlocking material to resume the predetermined shape after being engaged and disengaged from a mating, complementary interlocking material. Suitable hook material may be molded or extruded of nylon, polypropylene or another suitable material. Suitable single-sided hook materials for the first or second fastening components are available from Velcro Industries B.V., Amsterdam, Netherlands or affiliates thereof, and are identified as Velcro HTH-829 with a unidirectional hook pattern and having a thickness of about 0.089 millimeters (3.5 mils) and HTH-851 with a unidirectional hook pattern and having a thickness of about 0.051 millimeters (2 mils).

With reference to FIG. 3, the first fastening components 82 and 83 are desirably located on the inner surface 28 of the training pant 20 in the back waist region 24. The first fastening components 82 and 83 are desirably positioned along the distal edge 68 of the side panels 34. The first fastening components 82 and 83 can be adhered to the side panels 34 by any means known to those skilled in the art such as adhesive bonds, sonic bonds or thermal bonds.

With reference to FIG. 2, the second fastening components 84 and 85 can be located on the outer surface 30 of the training pant 20 in the front waist region 22. The second fastening components 84 and 85 are sized to receive the first fastening components 82 and 83 and are desirably positioned along the side edges 36 of the absorbent chassis 32 abutting the front waist edge 38. The second fastening components 84 and 85 may be adhered to the outer cover 40 by any means known to those skilled in the art such as adhesive bonds, sonic bonds or thermal bonds. In an alternative embodiment, the training pant 20 includes only a single second fastening component disposed in the front waist region 22 for refastenably connecting to the first fastening components 82 and 83 (not shown). In a further alternative embodiment, the outer cover 40 and/or bodyside liner 42 functions as a second fastening component in that it comprises a material that is releasably engageable with the first fastening components 82 and 83. In other alternative embodiments, the first fastening components are located on the outer surface and the second fastening components are located on the inner surface. The second fastening components 84 and 85 are desirably rectangular, although they may alternatively be square, round, oval, curved or otherwise nonrectangularly shaped.

In particular embodiments, the first fastening components 82 and 83 can be spaced inward from the distal edge 68 and the end edges 70 and 72 in order to protect the wearer from irritation that might be caused by contact with the fastening component. Specifically, the first fastening components 82 and 83 can be spaced transversely inward from the distal edge 68 by about 1 to about 15 millimeters, particularly about 1 to about 5 millimeters, such as about 2 millimeters. Also, the first fastening components 82 and 83 can be spaced longitudinally inward from the leg end edge 70 and from the waist end edge 72 by about 2 millimeters or more, particularly about 5 millimeters or more, such as from about 5 to about 15 millimeters. Similarly, in the front waist region 22 the second fastening components 84 and 85 are desirably spaced transversely inward from the side edge 36 by about 1 to about 50 millimeters, particularly about 1 to about 10 millimeters, such as about 2 millimeters, and are longitudinally spaced inward from the end edge 45 by about 2 millimeters or more, particularly about 5 millimeters or more, such as from about 5 to about 15 millimeters. The degree of spacing balances the fact that a smaller distance is harder for children and parents to remove but provides a more garment-like appearance, while a larger distance is easier for children and parents to remove but provides a loose and floppy appearance that is not garment-like.

When the first and second fastening components 82–85 are releasably engaged, the side edges 36 of the absorbent chassis 32 in the crotch region 26 define the leg openings 52, and the waist edges 38 of the absorbent chassis, including the outer edges 72 of the side panels, define the waist opening 50. When connected, the fastening components 82–85 form a refastenable seam 88 (FIG. 1) that is constructed to provide differential levels of securement, and more particularly to provide the greater levels of securement at the points along the refastenable seam that are likely to experience higher concentrations of separation forces.

The refastenable seams 88 desirably extend substantially the entire distance between the waist opening 60 and the leg openings 52 when the fastening components 82–85 are engaged. More specifically, the refastenable seams 88 can cover about 80 to 100 percent, and particularly about 90 to about 98 percent, of the distance between the waist opening 50 and each leg opening 52, which distance is measured parallel to the longitudinal axis 48 To construct the seams 88 to extend substantially the entire distance between the waist and leg openings 50 and 52, the fastening components 82 and 83 that are disposed on the side panels 34 can be formed to cover about 80 to 100 percent, and more particularly about 90 to about 98 percent, of the distance between the waist end edge 70 and the leg end edge 72 of the side panels.

Figure 4:
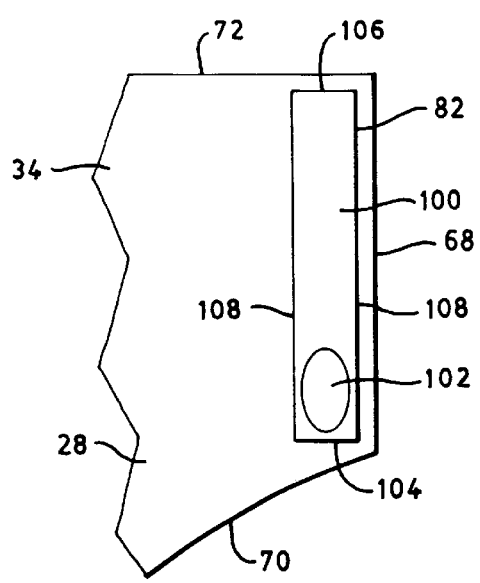
FIG. 4 illustrates an enlarged plan view of a side panel of the absorbent article shown in FIG. 1, and showing the surface of the article that faces the wearer when the article is worn.

FIG. 4 is an enlarged plan view of the inner surface 28 of one side panel 34 of the training pant 20. The illustrated first fastening component 82 comprises a primary region 100 and a secondary region 102 that have different releasable engagement properties. The first fastening component 82 defines an inner end edge 104 disposed toward the inner edge 70 of the side panel 34 and thus disposed toward one of the leg openings 52 when the fastening components are engaged, and an outer end edge 106 disposed toward the outer edge 72 of the side panel and thus disposed toward the waist opening 50 when the fastening components are engaged. The first fastening component 82 also defines opposite side edges 108 that extend between the inner and outer end edges 104 and 106.

In particular embodiments, each of the first fastening components 82 and 83 and the second fastening components 84 and 85 defines a length dimension that is aligned generally parallel with the longitudinal axis 48 of the training pant 20 and a width dimension that is aligned generally parallel with the transverse axis 49 of the training pant. For a child of about 9 to about 15 kilograms (20–30 pounds), for example, the length dimension of the fastening components is desirably from about 5 to about 13 centimeters, such as about 10 centimeters, and the width dimension is desirably from about 0.5 to about 3 centimeters, such as about 2 centimeters. The fastening components desirably have a length-to-width ratio of about 2 or greater, such as about 2 to about 25, and particularly about 5 or greater, such as about 5 to about 8. Alternatively, the fastening components and refastenable seams may be curved or otherwise non-linear.

The primary region 100 comprises fastening materials that provide a basic level of securement to the second fastening components 84 and 85, whereas the secondary region 102 comprises fastening materials that provide an augmented level of securement to the second fastening components. Stated differently, the secondary region 102 has greater releasable engagement properties relative to the second fastening components 84 and 85 than does the primary region 100. As shown in FIG. 4, the secondary region 102 is offset toward the inner end edge 104 of the of the first fastening component 82 and is laterally surrounded by the primary region 100.

Figure 6:
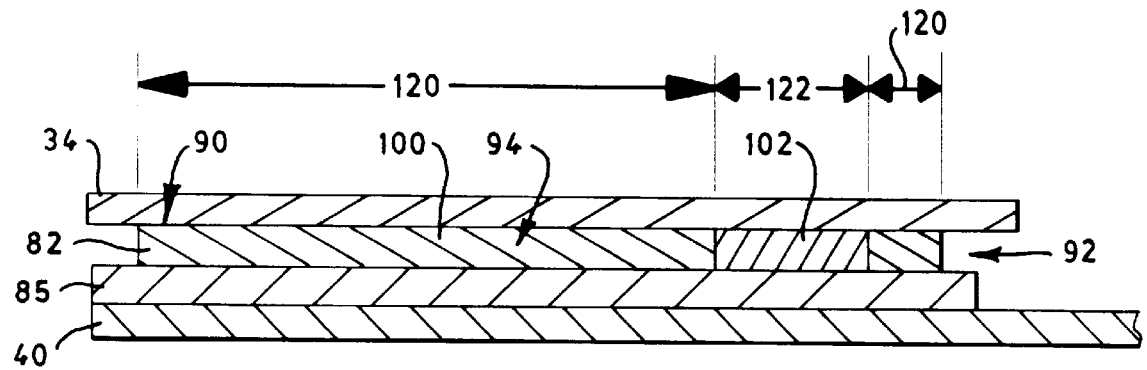
FIG. 6 schematically illustrates an enlarged section view taken in the plane of the line 6—6 in FIG. 5.
Figure 5:
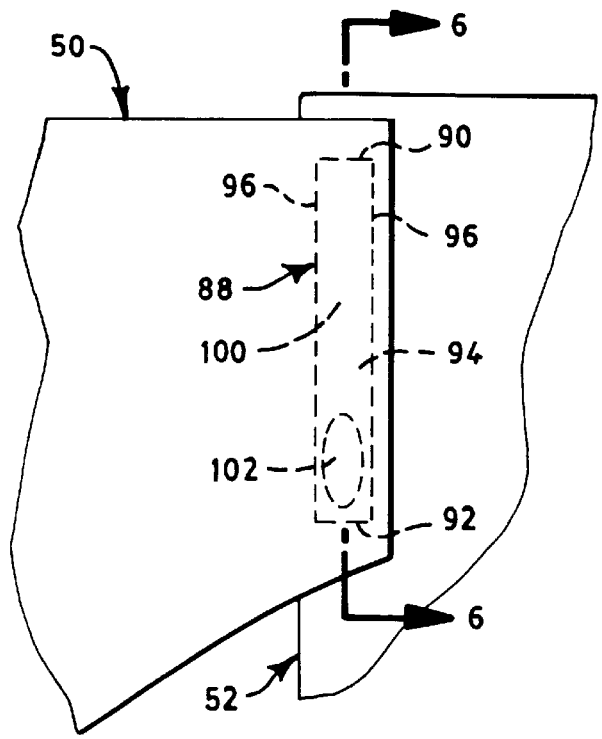
FIG. 5 illustrates one portion of the absorbent article where the fastener components are secured together to form the refastenable seam.

An enlarged region of the training pant 20 illustrating fastening components 82 and 85 secured together to form the refastenable seam 88 is shown in FIG. 5. A greatly enlarged section view taken through the longitudinal centerline of the fastening components is shown in FIG. 6. The refastenable seam 88 has a waist opening end 90 disposed toward the waist opening 50 of the training pant 20 and an opposite leg opening end 92 disposed toward one of the leg openings 52. A central portion 94 of the refastenable seam 88 is disposed intermediate the waist opening and leg opening ends 90 and 92. Side edges 96 (FIG. 5) of the refastenable seam 88 are oriented generally parallel to the longitudinal axis 48 of the training pant 20.

The waist opening and leg opening ends 90 and 92 of the refastenable seam 88 are considered to be the most remote regions of the seam, toward the waist opening 50 or leg openings 52 of the pant 20, respectively, where the first and second fastening components releasably engage one another.

The primary region 100 of the first fastening component 82 releasably engages the second fastening component 85 to form a main refastenable attachment zone 120. The main refastenable attachment zone 120 provides a basic level of securement between the first and second fastening components 82 and 85.

The secondary region 102 of the first fastening component 82 releasably engages the second fastening component 85 to form an enhanced refastenable attachment zone 122. The enhanced refastenable attachment zone 122 provides an augmented level of securement between the first and second fastening components 82 and 85. The augmented level of securement is desirably greater than the basic level of securement. The primary and secondary regions 100 and 102 are located at different longitudinal positions along the fastening components, measured parallel to the longitudinal axis 48 of the training pant 20.

Figure 7:
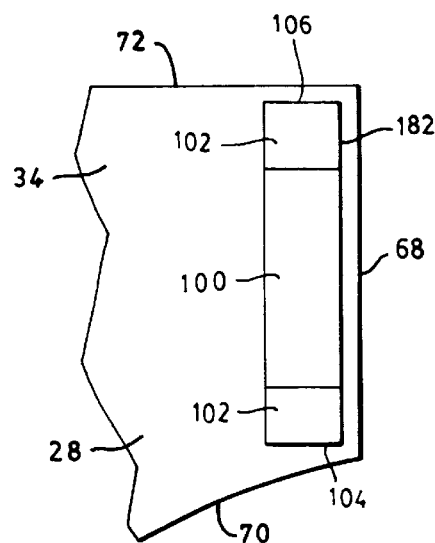
FIG. 7 illustrates an enlarged plan view similar to FIG. 4, but showing an alternative fastening component.

An alternative fastening component 182 is illustrated in FIG. 7. The first fastening component 182 includes a primary region 100 and a pair of secondary regions 102. One of the secondary regions 102 is disposed toward the inner end edge 104 of the first fastening component 182 and the other secondary region is disposed toward the outer end edge 106 of the first fastening component. The primary region 100 is interposed between the two secondary regions 102.

Figure 8:
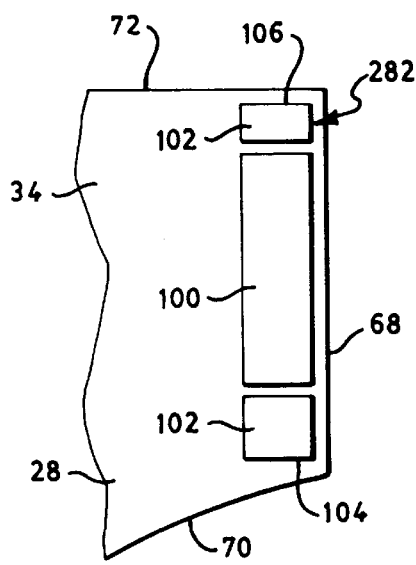
FIG. 8 illustrates an enlarged plan view similar to FIG. 4, but showing a further alternative fastening component.

The first fastening component 182 as illustrated in FIG. 7, when releasably engaged with the second fastening component 85, forms a refastenable seam 88 (not shown) having enhanced refastenable attachment zones 122 disposed toward the waist opening end 90 and the leg opening end 92 of the refastenable seam. A first fastening component 282 is shown in FIG. 8 that is similar to the fastening component 182 shown in FIG. 7 although formed of individual fastening materials.

In one aspect of the invention, the side panels 34 may comprise a plurality of segments, some of which have different elastic properties. For example, longitudinally offset segments near the inner edge 70 and near the outer edge 72 may provide greater tensions at a given elongation compared to an intermediate segment of the side panel. The different segments may be formed by a variety of methods, such as the incorporation of different amounts, types, orientation of elastic material, or the like. Desirably, the configuration of the fastening components can be matched to the tension properties of the various segments of the side panel. Thus, primary regions 100 may be positioned at longitudinal locations corresponding to segments of the side panel that provide a relatively lower level of tension and secondary regions 102 may be positioned at longitudinal locations corresponding to segments of the side panel that provide a relatively higher level of tension.

Figure 9:
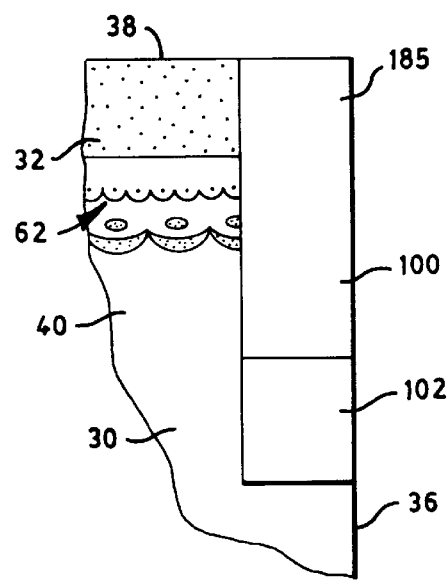
FIG. 9 illustrates another enlarged plan view similar to FIG. 4, but showing a still further alternative fastening component.

FIG. 9 illustrates a second fastening component 185 similar to that shown in FIG. 2. The second fastening component 185 of FIG. 9 includes a primary region 100 and a secondary region 102 that have different releasable engagement properties.

The training pant 20 may further include releasable side bonds (not shown) for improved reliability of maintaining the pant in a prefastened condition particularly when it is being pulled on or off over the hips of the wearer. Such releasable side bonds are desirably configured to be readily broken such that the caregiver can easily remove the training pant 20 after it has been soiled. The releasable side bonds desirably comprise ultrasonic point bonds. Absorbent articles including such releasable side bonds are further described in U.S. patent application Ser. No. 09/100,574 titled "Disposable Absorbent Articles Having Passive Side Bonds And Adjustable Fastening Systems" filed Jun. 19, 1998 by Elsberg, which is incorporated herein by reference.

The methods of the different aspects of the present invention are directed at reliably and consistently providing the refastenable training pant 20 as described herein and representatively illustrated in the Figures. The various components of the training pant 20 are integrally assembled together employing various types of suitable attachment means, such as adhesive, sonic and thermal bonds or combinations thereof.

The following EXAMPLE is provided to give a more detailed understanding of the invention. The particular amounts, proportions, compositions and parameters are meant to be exemplary, and are not intended to specifically limit the scope of the invention.

Twenty test fastening components representing one embodiment of the present invention were constructed. These fastening components comprised a loop material and a hook material having an adhesive applied in one region of the hook material. The fastening components were engaged with one another. The levels of engagement between the fastening components in the regions including and not including the adhesive were measured using the Peel Test described above.

The following materials were used in this Example:
1. Adhesive transfer tape measuring 2.5 cm. wide (1 inch) identified as SCOTCH® brand, 0.05 millimeter (2 mil) high performance adhesive transfer tape, from 3M, St. Paul, Minn. U.S.A.
2. Backing material formed of a spunbond-meltblown-spunbond laminate of polyolefin fibers with a meltblown content of approximately 14 weight percent, and an overall basis weight of 34 grams per square meter (1.0 osy).
3. Loop material identified as No. 36549 from Guilford Mills Inc., Greensboro, N.C., U.S.A.
4. Hook material formed in 1.9 cm. (0.75 inch) wide strips identified as VELCRO® hook HTH 851 with 2 mil backing, available from Velcro Industries B.V., Amsterdam, Netherlands or affiliates thereof.
5. Master Mechanic "All Temperature Glue Sticks" identified as 10.1 cm. by 1.1 cm. (4×7/16 inch) DT-6 mm 457-272, conforming to ASTM D4236 manufactured for TruServ, Chicago, Ill. 60631-3505, by FPC Corp. Purchased at Krueger Hardware, Neenah, Wis. U.S.A.

The following equipment was used in this Example:
1. Straight edge/ruler.
2. Brass roll, 5.0 cm. diameter (2 inch) by 5.7 cm. long (2.25 inch), 1,000 gram weight was marked on the roll, actual weight measured by the Mettler Scale was 982 grams.
3. Rotary cutter.
4. Paper cutter.
5. Master Mechanic "Professional Glue Gun" 80 watts HE 750 mm 456-613, manufactured for TruServ, Chicago, Ill. 60631-3503, by FPC Corp. Purchased at Krueger Hardware, Neenah, Wis. U.S.A.
6. Thermometer identified as a FLUKE $52^{k/j}$ Thermometer.
7. Scale identified as a Mettler PE 1600 scale.

The test samples were prepared according to the following procedure:
1. Attach the loop material (loop side up) to the backing material using the adhesive transfer tape. (100% coverage)
2. Lay the hook material (hook side down) on loop/backing material composite.
3. Use straight edge to cut 1.9 cm. wide (0.75 inch) strips of the hook/loop/backing material composite with the rotary cutter.
4. Use paper cutter to cut 7.6 cm. long (3 inch) strips.
5. Label the 7.6 cm. by 1.9 cm. (3×0.75 inch) strips with a sample number.
6. Let temperature stabilize in the hot melt applicator (glue gun) at about 385 to 390 degrees Fahrenheit. Use the thermometer to verify the temperature.
7. Weight sample strips on the Mettler Scale.
8. Peel back about 1.9 cm. (0.75 inch) of one end of the hook/loop/backing material composite strips separating the hook from the loop.
9. Apply a drop of adhesive from the glue gun on the hook, about 0.6 cm. (0.25 inch) from the end of the strip, being careful not to touch the adhesive nozzle to the hook because it is possible to burn through the hook material.
10. Immediately after applying the drop of adhesive fold the loop/backing material composite, back over the hook and roll 3 times with the 1,000 gram brass roll.
11. After all samples are made, re-weigh each strip to calculate the adhesive add-on.

The adhesive add-on of the twenty test fastening components was calculated to be 0.05 gram with a range of 0.03 to 0.06 grams. The Peel Test data from the twenty test samples is reported below in Table 1, with summary information provided in Table 2. The test inputs are provided in Table 3 below.

TABLE 1

|   | Peak Load (grams) | Average Load (grams) |
|---|---|---|
| 1 | 4084.2 | 121.5 |
| 2 | 3887.1 | 114.7 |
| 3 | 3907.4 | 129.6 |
| 4 | 2825.4 | 131.7 |

TABLE 1-continued

| | Peak Load (grams) | Average Load (grams) |
|---|---|---|
| 5 | 2701.5 | 143.5 |
| 6 | 3441.3 | 93.6 |
| 7 | 3912.4 | 91.7 |
| 8 | 3222.2 | 129.0 |
| 9 | 3775.5 | 110.4 |
| 10 | 3852.3 | 115.3 |
| 11 | 4039.2 | 112.3 |
| 12 | 3885.2 | 159.9 |
| 13 | 3203.0 | 159.4 |
| 14 | 3266.9 | 156.1 |
| 15 | 3302.4 | 160.0 |
| 16 | 4184.0 | 136.8 |
| 17 | 3432.0 | 121.6 |
| 18 | 3349.0 | 84.2 |
| 19 | 3819.3 | 74.6 |
| 20 | 4357.7 | 162.1 |

TABLE 2

| | Peak (grams) | Average (grams) |
|---|---|---|
| Mean | 3622.4 | 125.4 |
| Min | 2701.5 | 74.6 |
| Max | 4357.7 | 162.1 |
| Stdv | 450.4 | 26.6 |
| % Cov | 12.4 | 21.2 |

TABLE 3

| Crosshead Speed | 500.00 | Mm/Min |
|---|---|---|
| Load Limit HI | 10 | Kg |
| Brk Sensitivity | 110 | % |
| End of Test | 5.25 | Inch |

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. An absorbent article defining a longitudinal axis, a transverse axis, first and second longitudinally spaced waist regions, and a crotch region which extends between and interconnects the first and second waist regions, the absorbent article comprising an absorbent chassis and a fastening system, the fastening system comprising at least one first fastening component attached to the absorbent chassis and disposed in the first waist region and at least one second fastening component attached to the absorbent chassis and disposed in the second waist region, the first and second fastening components together defining a refastenable, variable-location seam defining a length dimension aligned generally parallel with the longitudinal axis and a width dimension aligned generally parallel with the transverse axis, the refastenable, variable-location seam having a main refastenable attachment zone providing a basic level of securement and an enhanced refastenable attachment zone providing an augmented level of securement that is greater than the basic level of securement, the main and enhanced refastenable attachment zones located at different longitudinal positions along the length dimension.

2. The absorbent article of claim 1, wherein the refastenable, variable-relocation seam has a length-to-width ratio of about 2 or greater.

3. The absorbent article of claim 2, wherein the refastenable, variable-location seam has a length-to-width ratio of about 5 or greater.

4. The absorbent article of claim 1, wherein the absorbent article defines a waist opening and leg openings when the first and second fastening components are releasably engaged, and the enhanced refastenable attachment zone is disposed adjacent a leg opening.

5. The absorbent article of claim 1, wherein the absorbent article defines a waist opening and leg openings when the first and second fastening components are releasably engaged, and the enhanced refastenable attachment zone is disposed adjacent the waist opening.

6. The absorbent article of claim 1, wherein the absorbent article defines a waist opening and leg openings when the first and second fastening components are releasably engaged, and the refastenable, variable-location seam comprises a pair of enhanced refastenable attachment zones that are disposed adjacent the waist opening and disposed adjacent a leg opening with the main refastenable attachment zone disposed therebetween.

7. An absorbent article defining a longitudinal axis, a transverse axis, a first waist region, an opposite second waist region, and a crotch region which extends between and interconnects the first and second waist regions, the absorbent article comprising at least one first fastening component disposed in the first waist region and at least one second fastening component disposed in the second waist region, the first and second fastening components adapted to releasably engage one another at a refastenable, variable-location seam having a length dimension aligned generally parallel with the longitudinal axis and a width dimension aligned generally parallel with the transverse axis, the first fastening component comprising a primary region and a secondary region that have different releasable engagement properties and are located at different longitudinal positions along the length dimension.

8. The absorbent article of claim 7, wherein the first and second fastening components comprise hook-and-loop materials and the primary and secondary regions comprise different types of hook materials.

9. The absorbent article of claim 7, wherein the first and second fastening components comprise hook-and-loop materials and the primary and secondary regions comprise different types of loop materials.

10. The absorbent article of claim 7, wherein the first and second fastening components comprise hook-and-loop materials and the secondary region further comprises an adhesive material.

11. The absorbent article of claim 10, wherein the adhesive material comprises about 1 gram per square centimeter or less of adhesive.

12. The absorbent article of claim 7, wherein the first and second fastening components comprise adhesive fasteners and the primary and secondary regions comprise different types of adhesive materials.

13. The absorbent article of claim 7, wherein the first fastening component is disposed in a back waist region of the absorbent article and the second fastening component is disposed in an opposite front waist region of the absorbent article.

14. The absorbent article of claim 7, wherein the first fastening component defines a length dimension aligned generally parallel with the longitudinal axis of the absorbent article and a width dimension aligned generally parallel with the transverse axis of the absorbent article.

15. The absorbent article of claim 14, wherein the first fastening component has a length-to-width ratio of about 2 or greater.

16. The absorbent article of claim 14, wherein the first fastening component has a length-to-width ratio of about 5 or greater.

17. The absorbent article of claim 7, wherein the absorbent article defines a waist opening and leg openings when the first and second fastening components are releasably engaged, the first fastening component defines an inner end edge disposed toward a leg opening and an outer end edge disposed toward the waist opening, the secondary region having greater releasable engagement properties than the primary region and the secondary region being offset toward the inner end edge of the first fastening component.

18. The absorbent article of claim 7, wherein the absorbent article defines a waist opening and leg openings when the first and second fastening components are releasably engaged, the first fastening component defines an inner end edge disposed toward a leg opening and an outer end edge disposed toward the waist opening, the secondary region having greater releasable engagement properties than the primary region and the secondary region being offset toward the outer end edge of the first fastening component.

19. The absorbent article of claim 7, wherein the absorbent article defines a waist opening and leg openings when the first and second fastening components are releasably engaged, the first fastening component defines an inner end edge disposed toward a leg opening and an outer end edge disposed toward the waist opening, the first fastening component comprising a pair of secondary regions that have greater releasable engagement properties than the primary region, the secondary regions being offset toward the opposite inner end edge end and the outer end edge of the first fastening component with the primary region disposed therebetween.

20. The absorbent article of claim 7, wherein the variable-location seam has a main refastenable attachment zone providing a basic level of securement and an enhanced refastenable attachment zone providing an augmented level of securement that is greater than the basic level of securement.

21. An absorbent article defining a longitudinal axis, a transverse axis, a first waist region, an opposite second waist region, and a crotch region which extends between and interconnects the first and second waist regions, the absorbent article comprising at least one first fastening component disposed in the first waist region and at least one second fastening component disposed in the second waist region, the first and second fastening components adapted to releasably engage one another at a refastenable, variable-location seam, the first fastening component comprising primary and secondary regions that have different releasable engagement properties, wherein the second fastening component also comprises primary and secondary regions that have different releasable engagement properties.

22. An absorbent article defining a longitudinal axis, a transverse axis, first and second longitudinally spaced waist regions, and a crotch region which extends between and interconnects the first and second waist regions, the absorbent article comprising an absorbent chassis and a fastening system, the fastening system comprising at least one first fastening component attached to the absorbent chassis and disposed in the first waist region and at least one second fastening component attached to the absorbent chassis and disposed in the second waist region, the first and second fastening components comprising mechanical fastening elements having a plurality of upwardly extending engaging elements and further comprising an adhesive disposed on at least some of the upwardly extending engaging elements, the first and second fastening components together defining a refastenable, variable-location seam having a main refastenable attachment zone providing a basic level of securement and an enhanced refastenable attachment zone containing the adhesive and providing an augmented level of securement that is greater than the basic level of securement.

23. The absorbent article of claim 22, wherein the absorbent article defines a waist opening and leg openings when the first and second fastening components are releasably engaged, and the enhanced refastenable attachment zone is disposed adjacent a leg opening.

24. The absorbent article of claim 22, wherein the absorbent article defines a waist opening and leg openings when the first and second fastening components are releasably engaged, and the enhanced refastenable attachment zone is disposed adjacent the waist opening.

25. The absorbent article of claim 22, wherein the absorbent article defines a waist opening and leg openings when the first and second fastening components are releasably engaged, and the refastenable seam comprises a pair of enhanced refastenable attachment zones that are disposed adjacent the waist opening and disposed adjacent a leg opening with the main refastenable attachment zone disposed therebetween.

26. The absorbent article of claim 22, wherein the main refastenable attachment zone comprises about 95 percent or less of a length dimension of the refastenable seam and the enhanced refastenable attachment zone comprises about 20 percent or less of the length dimension of the refastenable seam.

27. The absorbent article of claim 22, wherein the adhesive forms a refastenable bond.

28. An absorbent article defining a longitudinal axis, a transverse axis, first and second longitudinally spaced waist regions, and a crotch region which extends between and interconnects the first and second waist regions, the absorbent article comprising an absorbent chassis and a fastening system, the fastening system comprising at least one first fastening component attached to the absorbent chassis and disposed in the first waist region and at least one second fastening component attached to the absorbent chassis and disposed in the second waist region, the first and second fastening components comprising mechanical fastening elements having a plurality of upwardly extending engaging elements and further comprising an adhesive disposed on at least some of the upwardly extending engaging elements, the first and second fastening components together defining a refastenable, variable-location seam having a main refastenable attachment zone providing a basic level of securement and an enhanced refastenable attachment zone providing an augmented level of securement that is greater than the basic level of securement, wherein the absorbent article defines a waist opening and leg openings when the first and second fastening components are releasably engaged, and the refastenable seams cover about 90 to about 98 percent of the distance between the waist opening and the leg openings.

29. An article defining a longitudinal axis, a transverse axis, first and second longitudinally spaced waist regions, and a crotch region which extends between and interconnects the first and second waist regions, the article comprising a chassis and a fastening system, the fastening system comprising at least one first fastening component attached to the chassis and disposed in the first waist region and at least one second fastening component attached to the chassis and disposed in the second waist region, the first and second fastening components together defining a refastenable, variable-location seam defining a length dimension aligned generally parallel with the longitudinal axis and a width dimension aligned generally parallel with the transverse axis, the refastenable, variable-location seam having a main refastenable attachment zone providing a basic level of securement and an enhanced refastenable attachment zone providing an augmented level of securement that is greater than the basic level of securement, the main and enhanced refastenable attachment zones located at different longitudinal positions along the length dimension.

30. The article of claim 29, wherein the refastenable, variable-location seam has a length-to-width ratio of about 5 or greater.

31. An article defining a longitudinal axis, a transverse axis, a first waist region, an opposite second waist region, and a crotch region which extends between and interconnects the first and second waist regions, the article comprising at least one first fastening component disposed in the first waist region and at least one second fastening component disposed in the second waist region, the first and second fastening components adapted to releasably engage one another at a refastenable, variable-location seam having a length dimension aligned generally parallel with the longitudinal axis and a width dimension aligned generally parallel with the transverse axis, the first fastening component comprising a primary region and a secondary region that have different releasable engagement properties and are located at different longitudinal positions along the length dimension.

32. The article of claim 31, wherein the first fastening component defines a length dimension aligned generally parallel with the longitudinal axis of the article and a width dimension aligned generally parallel with the transverse axis of the article, wherein the first fastening component has a length-to-width ratio of about 5 or greater.

* * * * *